US 6,902,564 B2
Jun. 7, 2005

(54) METHODS AND DEVICES FOR ELECTROSURGERY

(76) Inventors: Roy E. Morgan, 867 Hummingbird Dr., San Jose, CA (US) 95125; Wayne K. Auge, II, 936 Vista Jemez Ct., Santa Fe, NM (US) 87505; N. Mani Prakash, 576 Virginia Ave., Campbell, CA (US) 94043

(*) Notice: Subject to any disclaimer, the term of this patent is extended or adjusted under 35 U.S.C. 154(b) by 125 days.

(21) Appl. No.: 10/119,671

(22) Filed: Apr. 9, 2002

(65) Prior Publication Data

US 2003/0036753 A1 Feb. 20, 2003

Related U.S. Application Data

(60) Provisional application No. 60/312,965, filed on Aug. 15, 2001.

(51) Int. Cl.$^7$ .............................................. A61B 18/04
(52) U.S. Cl. .............................. 606/32; 606/41; 606/45; 606/49
(58) Field of Search .............................. 606/32, 41, 45, 606/49

(56) References Cited

U.S. PATENT DOCUMENTS

| | | | |
|---|---|---|---|
| 4,014,777 A | 3/1977 | Brown | |
| 5,494,538 A | 2/1996 | Kirillov et al. | |
| 5,514,130 A | * 5/1996 | Baker | 606/41 |
| 5,569,242 A | * 10/1996 | Lax et al. | 606/42 |
| 5,669,904 A | 9/1997 | Platt, Jr. et al. | |
| 5,683,366 A | 11/1997 | Eggers et al. | |
| 5,697,882 A | 12/1997 | Eggers et al. | |
| 5,746,896 A | 5/1998 | Shimamune et al. | |
| 5,840,166 A | 11/1998 | Kaneko | |
| 5,919,191 A | 7/1999 | Lennox et al. | |
| 5,964,968 A | 10/1999 | Kaneko | |
| 6,032,077 A | 2/2000 | Pomeranz | |
| 6,135,998 A | 10/2000 | Palanker | |
| 6,149,620 A | 11/2000 | Baker et al. | |
| 6,162,219 A | 12/2000 | Nilsson et al. | |
| 6,206,878 B1 | 3/2001 | Bishop et al. | |
| 6,213,999 B1 | 4/2001 | Platt, Jr. et al. | |
| 6,241,723 B1 | 6/2001 | Heim et al. | |
| 6,264,652 B1 | 7/2001 | Eggers et al. | |
| 6,309,387 B1 | 10/2001 | Eggers et al. | |
| 6,322,549 B1 | 11/2001 | Eggers et al. | |
| 6,383,184 B1 | * 5/2002 | Sharkey | 606/41 |
| 6,391,025 B1 | 5/2002 | Weinstein et al. | |

* cited by examiner

Primary Examiner—Lee S. Cohen
(74) Attorney, Agent, or Firm—Stephen A. Slusher; Peacock Myers & Adams P.C.

(57) ABSTRACT

Method and devices for electrosurgery by means of oxy-hydro combustion. Deleterious effects to tissue are minimized by means of control of acid-base shift reactions, which reactions can further be employed to control oxy-hydro combustion reactions. In one embodiment, radiofrequency energy in electrical connection with electrodes is employed to induce electrolysis in an aqueous salt environment, thereby producing oxygen and hydrogen, with the same energy source employed to initiate a combustion reaction.

24 Claims, 11 Drawing Sheets

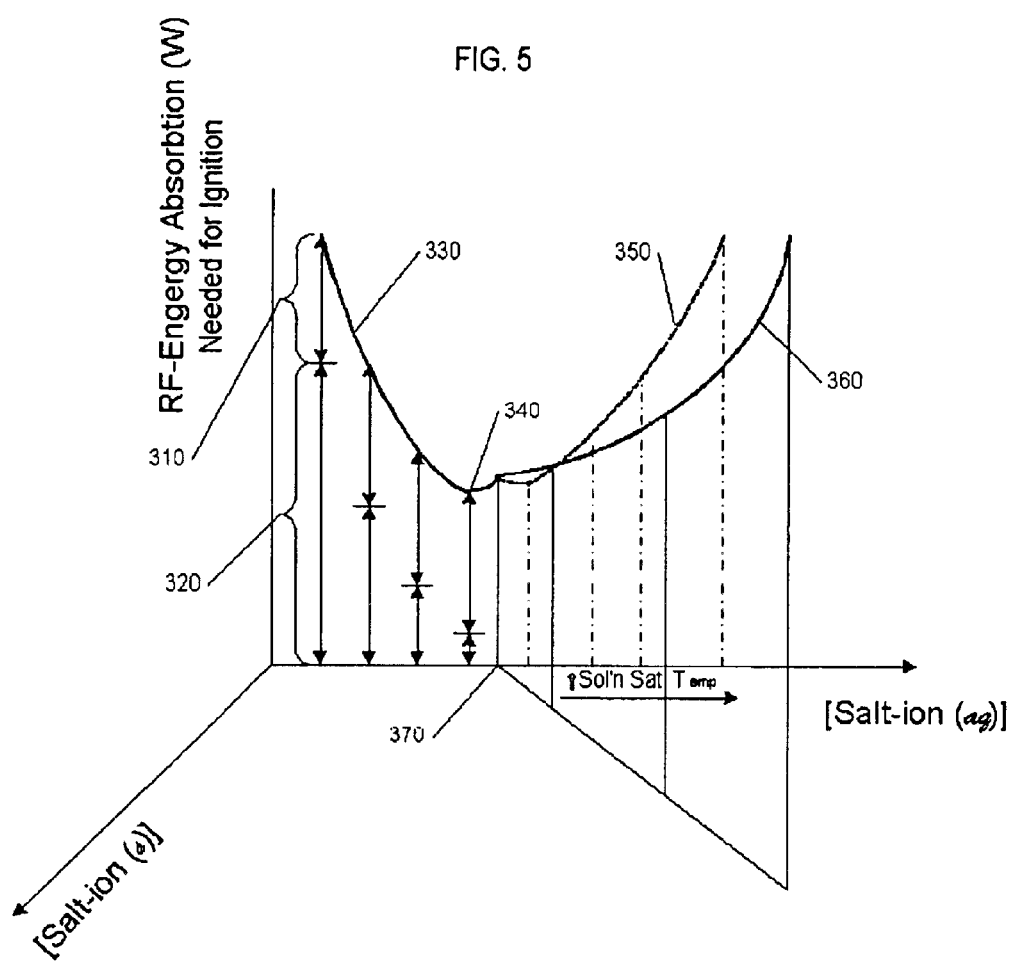

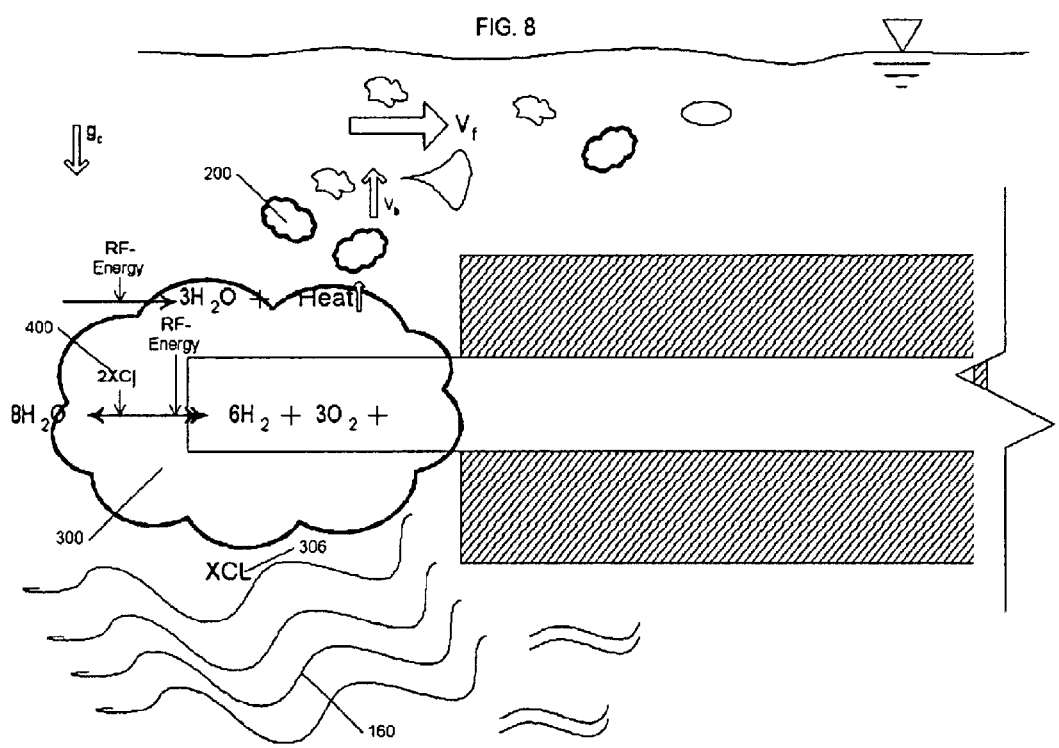

METHODS AND DEVICES FOR ELECTROSURGERY

CROSS-REFERENCE TO RELATED APPLICATIONS

This application claims the benefit of the filing of U.S. Provisional Patent Application Ser. No. 60/312,965, entitled System and Method of Electrosurgical Biologic Tissue Modification and Treatment Utilizing Oxy-Hydro Combustion—Acid Base Shift Reactions, filed on Aug. 15, 2001, and the specification thereof is incorporated herein by reference.

BACKGROUND OF THE INVENTION

1. Field of the Invention (Technical Field)

The present invention relates to methods and devices for electrosurgery, including devices that operate in a conductive media, including an aqueous conductive media, by means of oxygen and hydrogen combustion.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

A variety of electrosurgical devices, used for cutting, ablation, and the like in surgical procedures, are known. In general, it is claimed that these devices utilize mechanisms of action based on various plasma formation physiochemical paradigms. A plasma, broadly defined as "the fourth state of matter" as opposed to solids, liquids, and gases, is a state in which atoms have been broken down to form free electrons and stripped nuclei by the application of high energy or temperatures (ca. $10^6$ degrees). In a plasma, the charge of the electrons is balanced by the charge of the positive ions so that the system as a whole is electrically neutral. The energy input required to initiate a plasma is related to the initial state of the matter as a solid, liquid, or gas, the molecular bond energy, and the ease with which electrons can be stripped from their orbits, among other variables. The percent of the samples that actually become a plasma is usually very small due to the large energy requirements to create a plasma (i.e. ~0.1% of a mole). Further, a plasma can be constrained by magnetic fields lowering the input energy necessary. A sustainable plasma often requires a vacuum or magnetic field control since the plasma elements quickly seek to be grounded, quenching the plasma; however, some systems may form short duration plasmas on the order of nano- or micro-seconds depending upon energy input and degree of vacuum/magnetic field present.

Some prior art references disclose electrosurgical devices with claimed use of a gas plasma consisting of an ionized gas that is capable of conducting electrical energy. In certain of these devices, either ambient air or a supplied gas is used for ionization, such as the devices disclosed in U.S. Pat. Nos. 5,669,904, 6,206,878 and 6,213,999. If a gas is supplied, it is an inert gas such as argon. In general, these devices are intended for use in ambient atmosphere for the treatment of soft tissue.

Other electrosurgical devices function in liquid media and utilize some form of radiofrequency (RF) energy, such as with two or more electrodes. Heat is generated by use of the RF energy, resulting in destruction or ablation of tissues in proximity to the electrodes. Thus the devices may be employed for coagulation of blood vessels, tissue dissection, tissue removal, and the like. U.S. Pat. No. 6,135,998 teaches an electrosurgical probe immersed in liquid media or tissue, wherein an electrical pulse is applied, with the claimed result that "plasma streamers" are formed from the endface area of a first electrode. In this patent, it is claimed that cutting action results from the plasma streamers. The minimum voltage is on the order of 1.5–2.0 kV, with 15 kV being the preferred maximum voltage, at a minimum power dissipation of 500 Watts, and preferable a higher power dissipation of 800 to 1500 Watts.

Other lower energy electrosurgical devices are known, consisting of monopolar and bipolar configurations that function at energy configurations at or below 1.4 kV and 300 Watts. Both monopolar electrosurgical devices, in which the electrosurgical device includes an active electrode with a return electrode separately connected to the patient such that direct electric current flows through the patient's body, and bipolar electrosurgical devices, in which the electrosurgical device includes both active and return electrodes, are now well known in the art. These electrosurgical device configurations can be used in ambient air or in a fluid medium. In general, it has been believed that these electrosurgical devices generally operate by means of creation of a plasma or some related form of ionization. Thus prior art devices, such as that disclosed in U.S. Pat. No. 5,683,366, are claimed to rely on the fluid irrigant components participating in ionic excitation and relaxation, with attendant release of photonic energy. This mode of operation is often referred to as "utilizing a plasma". Prior art methods claiming an ionized vapor layer or plasma include, in addition to the patents disclosed above, the methods disclosed in U.S. Pat. Nos. 5,697,882, 6,149,620, 6,241,723, 6,264,652 and 6,322,549, among others.

A plasma requires that atoms be completely ionized to a gas of positive ions and electrons, and, if sustainable, would likely need to occur in a vacuum-like environment. It is unlikely that many, if not most, prior art devices generate a plasma even for a short time. This most notably follows from consideration of the overall energy balance required to initiate or sustain a plasma in either ambient air or aqueous, cellular, or other biologic environments. The nominal 200 to 1500 Watts of power normally employed in a typical electrosurgical device, or any other energy level or configuration contemplated for electrosurgical application (most, however, are between 200 and 300 Watts), is insufficient to initiate and/or sustain a plasma, even in a vacuum and with magnetic field control, even for a short period of time. For example, in a saline solution typically utilized during electrosurgery, 49.6 kW-s/mole (I eV=5.13908; II eV=47.2864; III eV=71.6200; etc.) is needed to ionize sodium, while the ionization energy of simple water is 12.6206 eV (i.e. one electron volt=$1.602177 \times 10^{-19}$ Joules) as referenced in *CRC Handbook of Chemistry and Physics*, 72 ed., Lide, David R., CRC Press, 1991. The energy to initiate a plasma typically exceeds the ionization potential of a material, and to sustain a plasma requires an even greater energy input. Further, once ions have been formed in solution, such as in an aqueous solution of sodium as employed in electrosurgery, a yet even greater energy input is required.

Further, many prior art electrosurgical references ignore recognized phenomena relating to plasmas, such as the large ionization potentials and energy necessary to initiate a plasma or to sustain a plasma and the role of the vacuum or magnetic fields in such circumstances. Most electrosurgical devices cannot deliver the energy required to initiate, let alone sustain, a plasma; and, further, electrosurgical applications do not occur in a vacuum environment or in a magnetically controlled environment. The energy needed to create a plasma in vivo during electrosurgery would overwhelm the ability of the host organism to withstand such an energy insult globally. Plasma cutters as used in metal fabrication are examples of the high energy necessary to "utilize a plasma" at normal pressures; yet such high energy levels certainly have not been contemplated for electrosurgical application due to the significant iatrogenic damage that would occur. This understanding has led us to search for other physiochemical paradigms to understand electrosurgery as it is practiced at energy configurations amenable and safe for in vivo application and to more fully and correctly explain common physiochemical observations during electrosurgery in order to create more appropriate electrosurgical devices and methods.

In industrial settings, it is known to employ an oxygen and hydrogen combustion reaction, such that a "water torch" results by ignition of co-mingled oxygen and hydrogen gas molecules liberated from water through high frequency electrolysis, as is disclosed in U.S. Pat. No. 4,014,777. However, such methods have never been intentionally applied to medical procedures, such as for electrosurgical devices and methods. Further, such devices and methods have never been optimized for the constraints of use of electrosurgical devices on biologic tissue, including constraints resulting from the presence of discrete quantities of electrolyte fluids, the presence of physiologic fluids and materials, the desires to minimize collateral tissue injury, the need to avoid generation of toxic by-products, the attendant host organism tissue response, and the like.

There is thus a need for electrosurgical devices that are optimized to the true physical and chemical processes involved in the operation and use of such electrosurgical devices upon biologic tissue within this energy spectrum and power range.

SUMMARY OF THE INVENTION
(DISCLOSURE OF THE INVENTION)

In one embodiment, the invention provides a method of performing an electrosurgical procedure on a patient, the method including the steps of providing a surgical probe including an active electrode and a return electrode separated by an insulator, providing an aqueous salt ion environment at the location wherein the electrosurgical procedure is to be performed, the environment comprising sufficient volume to permit immersion of at least the portion of the surgical probe including the active electrode and return electrode, and applying current to a circuit comprising the active electrode and return electrode, the current being less than that required to induce plasma ionization, whereby the application of current induces electrolysis of a portion of the aqueous salt ion environment thereby producing hydrogen and oxygen and further initiates a hydrogen and oxygen combustion reaction. In this method, the active electrode may include an alloy that induces release of hydrogen, including but not limited to alloys such as a magnesium alloy or a rare earth metal and nickel alloy. The aqueous salt ion environment described in the method may include a salt ion such as an ionic form of sodium chloride, calcium chloride, magnesium bromide, magnesium iodide, potassium iodide, potassium chloride, lithium bromide or lithium chloride. In the practice of the method, the current applied may include a high frequency voltage difference, such as radiofrequency (RF) energy. The insulator in the method may consist of an electrical and thermal insulator. The aqueous salt ion environment may include naturally occurring biological fluids of the patient, or may include an exogenous aqueous salt ion solution.

In another embodiment of the invention, a method is provided for inducing a therapeutic response in living tissue while minimizing deleterious acid-base shifts in the living tissue, the method including the steps of providing a probe including an active electrode and a return electrode separated by an insulator, the active electrode being disposed within an elongated lumen, providing an aqueous salt ion solution at the site wherein the therapeutic response is desired, the solution comprising sufficient volume to permit immersion of at least the portion of the probe including the active electrode disposed within the elongated lumen and the return electrode, positioning the active electrode in close proximity to the location wherein the therapeutic response is desired, the active electrode and return electrode being immersed in the aqueous salt ion solution, and applying a high frequency voltage between the active electrode and return electrode, the voltage being less than that required to induce plasma ionization. In this method, acid-base shifts resulting from application of the high frequency voltage may be partially contained within the lumen. The active electrode and return electrode separated by an insulator may be disposed within the elongated lumen, and optionally the position of the active electrode along the long axis of the lumen is adjustable. By this means, the method may include controlling the desired therapeutic response by adjusting the position of the active electrode along the long axis of the lumen. By means of the practice of the method, minimal tissue necrosis is induced at the site wherein the therapeutic response is desired. The active electrode employed in this method may further include an alloy that induces release of hydrogen, such as a magnesium alloy or a rare earth metal and nickel alloy. The aqueous salt ion solution employed in this method may include a salt ion of sodium chloride, calcium chloride, magnesium bromide, magnesium iodide, potassium iodide, potassium chloride, lithium bromide or lithium chloride. The high frequency voltage may include radiofrequency (RF) energy. The insulator may include an electrical and thermal insulator. The therapeutic response obtained by means of the method may include nerve ablation, tissue ablation, tissue cutting, tissue coagulation, tissue modification, or induction of host healing response.

In another embodiment the invention provides a method for decreasing tissue necrosis at a site wherein high frequency voltage is applied to an active electrode immersed in an aqueous salt ion solution, the method including means for minimizing the acid-base shift at the site. In the practice of the method, the acid-base shift at the site does not cause deleterious alterations in tissue at the site. The means for minimizing the acid-base shift at the site can include application of high frequency voltage less than that required to induce plasma ionization. Such means for minimizing the acid-base shift at the site can alternatively include application of high frequency voltage to an active electrode disposed within an elongated lumen, the active electrode being proximal the site. The active electrode may be movably disposed along the long axis within the elongated lumen, with the method further providing for minimizing the acid-base shift at the site by adjusting the position of the active electrode along the long axis of the lumen.

In another embodiment the invention provides an apparatus for performing surgical procedures, the apparatus including first and second gas delivery channels disposed within an elongated housing having a proximal and distal end, first and second gas connectors at the proximal end for connecting the first and second gas delivery channels to a first and second gas source, a gas mixing plenum chamber with an inlet and an outlet at the distal end of the elongated housing, the first and second gas delivery channels being in fluid connection with the inlet, and an active electrode connected to a current source, the active electrode proximal to the gas mixing plenum chamber outlet. The apparatus can further include a flame arrester positioned between the gas mixing plenum chamber outlet and the active electrode. The gas mixing plenum chamber outlet may further include an acceleration throat. The active electrode may include an alloy that induces release of hydrogen, such as a magnesium alloy or a rare earth metal and nickel alloy. The active electrode may include a gas porous structure. The apparatus may further include a return electrode, including those wherein the return electrode is in a fixed position proximal the active electrode.

In another embodiment the invention provides an electrosurgical apparatus including a housing having proximal and distal ends, an active electrode disposed adjacent the distal end of the housing, the electrode comprising an alloy that induces release of hydrogen, and an electrical connector extending from the active electrode to the proximal end of the housing for connecting the electrode to a source of current. In this apparatus, the alloy may be a magnesium alloy or a rare earth metal and nickel alloy. In the apparatus, the alloy may induce release of hydrogen upon the application of current.

In another embodiment of the invention, an electrosurgical apparatus is provided including an elongated lumen having proximal and distal ends, an active electrode adjustably positionable within and along the long axis of the lumen, and an electrical connector extending from the active electrode connecting the electrode to a source of current. In this apparatus there may further be provided a return electrode fixed in position relative to the active electrode. The elongated lumen may include an insulating material, which may be an electrically insulating material or a thermally insulating material. The active electrode may be movably adjustable within and along the long axis of the lumen during operation of the apparatus, and may be adjustably positionable beyond the distal end of the lumen. The distal end of the lumen may be in the shape or form of a segment of a cone, decreasing in diameter at the distal end.

In yet another embodiment of the invention, an apparatus for electrosurgery is provided including an active electrode, a return electrode fixed in position relative to the active electrode, and a radiofrequency power supply in electrical connection with the active electrode and return electrode, the power supply generating less radiofrequency power than that required to induce plasma ionization, whereby on immersion of the active electrode and return electrode in an aqueous salt ion environment, the application of radiofrequency power induces electrolysis of a portion of the aqueous salt ion environment, thereby producing hydrogen and oxygen, and further initiates a hydrogen and oxygen combustion reaction.

A primary object of the present invention is to provide an electrosurgical device that regulates the rate of combustion in underwater environments, such as combustion in aqueous, cellular and biologic environments.

Another object of the present invention is to provide an electrosurgical device that provides tissue dissection, ablation and the like by means of an oxy-hydro combustion reaction, wherein the oxygen and hydrogen are produced by means of electrolysis.

Another object of the present invention is to provide a device and methods that eliminate the need for use of an ionic solution, such as saline, to foster oxy-hydro combustion reactions at the surgical site.

Another object of the present invention is to provide for oxy-hydro combustion that utilizes the salt ion fluid of intra-cellular structures to sustain electrolysis and combustion.

Another object of the present invention is to provide for acid base shifts in micro-cellular probes that utilize the salt ion fluid of intra-cellular structures to regulate and sustain electrolysis and combustion.

Another object of the present invention is to employ electrodes that liberate a gas useful for combustion, such as hydrogen, upon the application of power to such electrode.

Another object of the present invention is to provide devices employing lower energy levels to achieve ignition of oxygen and hydrogen gases resulting from local hydrolysis, such ignition and subsequent combustion providing the desired tissue dissection, ablation and the like.

Another object of the present invention is to provide an electrosurgical device with lower energy requirements, thereby resulting in a lower net energy transfer to local tissue structures, whereby there are lower levels of collateral tissue damage.

Yet another object of the present invention is to provide an electrosurgical device that provides combustion gases, such as oxygen and hydrogen, as part of the electrosurgical device.

A primary advantage of the present invention is the ability to optimize ionic salt solutions for the oxy-hydro combustion reaction.

Another advantage of the present invention is the utilization of an acid-base throttle effect to regulate an electrosurgical device.

Another advantage of the present invention is the use of a wide range of different and novel salt solutions, in addition to the normal saline conventionally employed in electrosurgical procedures.

Yet another advantage of the present invention is the design and use of irrigants that that optimize electrolysis, optionally limit production of hazardous by-products, and further optionally produce by-products with efficacious benefits.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 5 is a graph depicting the acid-base throttle effect and its relation to salt concentration, energy imparted to the fluid, salt crystal precipitate partial fraction, and electrical conduction;

FIG. 8 is a view of the generalized flow in a non-salt aqueous environment including the physiochemistry of oxy-hydro combustion.

DESCRIPTION OF THE PREFERRED EMBODIMENTS

BEST MODES FOR CARRYING OUT THE INVENTION

The invention disclosed herein provides, in one embodiment, electrosurgical devices that operate in conductive media, such as an ionic aqueous media. The electrosurgical devices employ combustion, and preferably oxygen and hydrogen (oxy-hydro) combustion, as a mechanism for tissue dissection, ablation, cutting, coagulation, modification, treatment and the like. In one embodiment, oxygen and hydrogen are generated by electrolysis of the media, such as a saline media, endoscopy irrigant or physiologic tissue or cellular fluid, within which it occurs. In another embodiment, at least one of the gases oxygen or hydrogen can be generated by means of an electrode that, upon electrical excitation, releases such gas. In another embodiment, an external source of oxygen or hydrogen, and preferably both, may be utilized. In yet another embodiment, this reaction can be controlled and throttled by the local control of constituent acid-base physiochemical participants in the process. In the foregoing embodiments, electrical energy, such as a high frequency voltage difference, and preferably radiofrequency energy, can be employed to initiate oxy-hydro combustion and, in the embodiments so requiring, induce electrolysis of the media within which it functions or of the tissue to which it is applied to achieve the desired goals of electrosurgical treatment.

Figure 1:
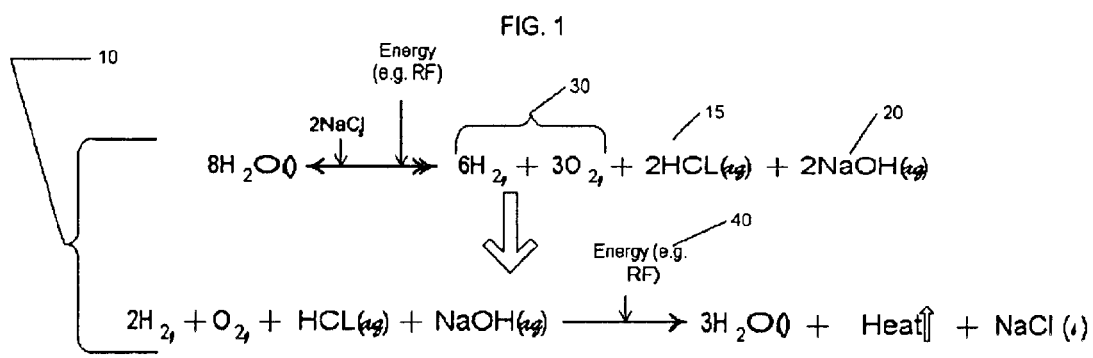
FIG. 1 is the stoichiometric chemical equation for chemical reactions related to the invention.

The equations of FIG. 1 illustrate the chemical equations that describe the overall oxy-hydro reaction, with associated acid-base shifts, resulting from hydrolysis of water and subsequent ignition of the resulting oxygen and hydrogen as disclosed herein. It is hypothesized that what has been traditionally thought of as the ordinary phenomenon of electrosurgery, namely "arcing", "electron excitation", "molecular friction", "vapor layer", "plasma formation", "plasma streamers", or "popping", may more properly be understood to be a result, in at least substantial part, of oxy-hydro combustion occurring within biologic constraints. The physiochemistry of the electrosurgical process is hypothesized to consist of an acid-base shift that governs the relative availability of the amount of water that can be consumed as part of a hydrolysis chemical reaction. The hydrolysis reaction is driven by the high frequency current flowing between active and return electrodes in both the bi-polar and mono-polar modes of operation of electrosurgical probes. This oxy-hydro combustion theory accounts for all necessary chemical and energy constituents that are present as well as the physical observations of light emission and heat generation during the use of such devices. The physiochemical occurrences of electrosurgery have not previously been reconciled into a single accurate and cohesive theory.

Chemical equations 10 generally govern the process herein disclosed, whereby the initial liberation of elemental oxygen and hydrogen gases 30 occurs by means of electrolysis. Given that the underwater electrosurgical process occurs in a salt solution, either externally applied or that of the tissue or cell itself, such as a 0.9% by weight saline solution, the true role of these elements should also be reconciled. The presence and true action of the salt, i.e. sodium chloride (NaCl) for example, can be accounted for by means of equations 10. The normal stoichiometry of the electrolysis reaction dictates that if elemental gas separation is occurring, then the solute participants must join with the remaining solution components of water to form a complementary acid-base pair. This pair is shown on the right-hand side of the upper half of equations 10 as hydrochloric acid 15 and sodium hydroxide 20 base pair. As is well known, hydrogen and oxygen gases 30 can be co-mingled without spontaneous exothermic reaction. A small amount of energy, such as RF energy 40, is required to overcome the nominally endothermic reaction and ignite the oxy-hydro combustion. Once ignited, the reaction will continue until all the reactants are consumed and reduced to the products shown on the right-hand side of the lower half of equations 10.

Figure 1A:
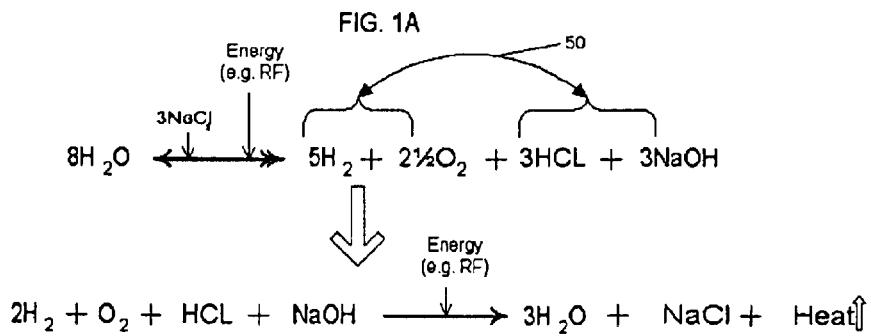
FIG. 1A is the equation for the acid-base "throttle" effect.

The equations of FIG. 1A illustrate the effect of the acid-base throttling reaction herein disclosed. The oxy-hydro combustion process depicted is dynamic and occurs in a fixed fluid reservoir, which necessarily results in dynamically changing concentrations of salt ions as a function of electrolytic conversion of water to elemental gas. This equation necessarily suggests that as the acid-base shift occurs in the reservoir, less and less water is available for hydrolysis. This phenomenon is seen in FIG. 1A where the acid-base pair is shown in increased molar proportion to the normal stoichiometric quantity of base reactions 10. The reduction of available water for hydrolysis is evident in the relationship 50 of oxygen and hydrogen gas to the acid-base pair. The finding is necessarily evident from the stoichiometry, namely that insufficient water is available given a fixed initial eight (8) moles of water, based on the finite reservoir of water, with increasing resulting molar concentrations of acid and base as oxygen and hydrogen are liberated from the solution in a gaseous state, such as by bubbling out of solution. As fewer moles of oxygen and hydrogen gas are present after hydrolysis as in FIG. 1A, the balancing portion of atoms account for the dynamic increase acid-base concentration.

Figure 1B:
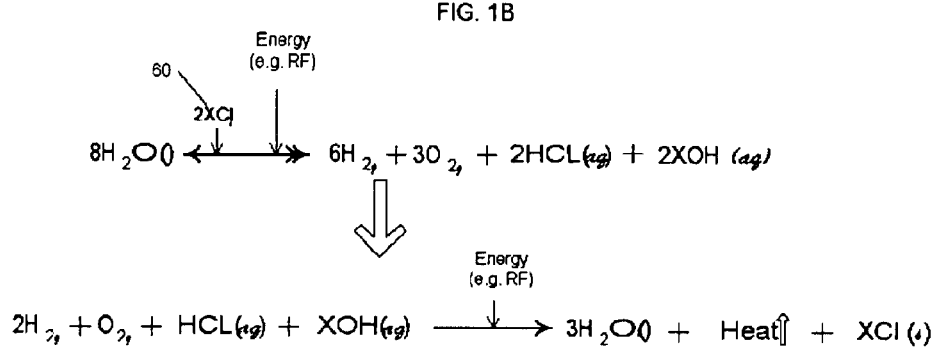
FIG. 1B is the equation for a generalized form of the oxy-hydro reaction process.

The equations of FIG. 1B demonstrate a more general case of the oxy-hydro combustion reaction process in which the ionic salt is represented by variable 60, where X is any appropriate group I, period 1–7 element of the periodic table. This generalized reaction illustrates how hydronium and hydroxide ions can contribute to the same overall chemical reaction known as oxy-hydro combustion.

Figure 1C:
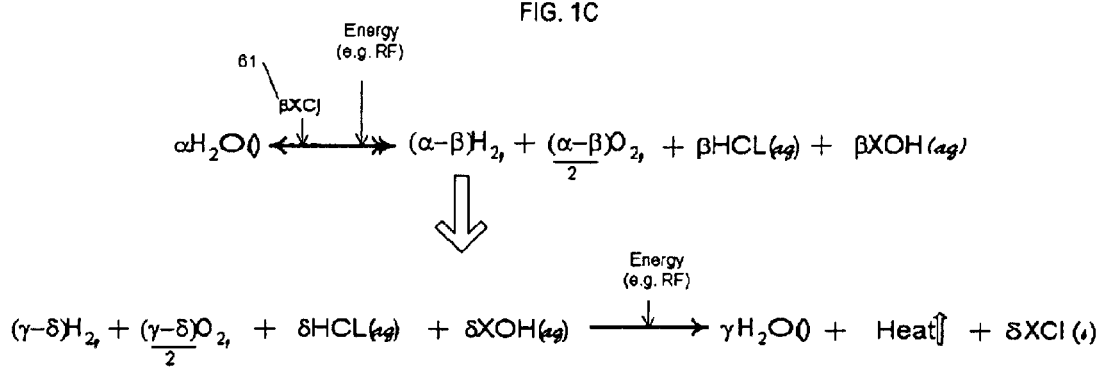
FIG. 1C is the equation for a generalized form of the oxy-hydro reaction process showing the effect of varying molar coefficients.

The equations of FIG. 1C demonstrate the more general case of the oxy-hydro combustion reaction process in which the ionic salt is represented by variables 61, consisting of $\alpha$, $\beta$, $\gamma$, and 67, wherein the molar quantities required for stoichiometric combustion are any value that appropriately satisfies the oxidation reduction valence requirements for the overall reaction. This generalized reaction case shows how oxygen and hydrogen requirements can vary and still result in the same overall chemical reaction known as oxy-hydro combustion.

The modes of oxy-hydro combustion operation described in FIG. 1, FIG. 1A and FIG. 1B depict theoretical stoichiometric reaction processes induced by application of high frequency electromagnetic energy to a salt ion solution, including salt ion solutions typically found within biologic tissues themselves. The fundamental process is governed by the rate of electrolysis in the initial dissociation of water into oxygen and hydrogen gas, as shown in equations 10.

Without wishing to be bound by theory, it is believed that the mechanism of action explaining operation of prior art electrosurgical devices is erroneous, and that an understanding and appreciation of the herein hypothesized correct mechanism of action results in devices and methods as further disclosed herein.

In prior art, it has been assumed that conventional bipolar electrosurgical devices utilize excitation and relaxation of salt ions resulting in photonic energy release such as through a plasma formation. The basis for such claims is that sufficient energy is imparted to the vaporized salt solution to provide electron shell excitation of the native sodium ions. Upon relaxation of the excited electron, a photon is emitted (a foundational concept of quantum theory as originally developed by Niels Bohr in 1913). However, the ionization energy per mole of Na is 496 kJ as referenced in the *CRC Handbook of Chemistry and Physics*, 72 ed., Lide, David R., CRC Press, 1991, pp. 210–211. This energy is the equivalent to 496,000 Watt-seconds/mole. Even if only one-tenth of a mole of Na is present, a net energy of 49.6 kW-s/mole is needed to ionize the sodium to form a plasma. This energy is far greater than the 200 to 1500 Watts of power provided by prior art conventional electrosurgical power supplies, methods, and devices.

Further, monopolar electrosurgical devices have been described as using a "molecular friction" phenomenon to generate an "arc." The implicit assumption of this paradigm is that the majority of the energy imparted by the wave/particle function of nominal waves created by the electrosurgical power supply and device is absorbed at the natural frequency of the salt ions. A process called "ionic agitation" to produce molecular friction, resulting from ions attempting to "follow" the changes in direction of alternating current, is used as one common description of the observed phenomenon as referenced in M. J. Medvecky, et al., Thermal Capsular Shrinkage Basic Science and Applications, *Arthroscopy: The Journal of Arthroscopic and Related Surgery*, 2001; 17:624–635. However, ordinary microwave technology demonstrates that higher frequencies are needed to excite water, including salt water, as well as the ions normally contained within biologic tissue. Additionally, understanding how ions from a salt exist in solution makes it unlikely that the claimed excitations result in the observed phenomenon. A normal saline solution consists of sodium chloride (NaCl) salt dissolved in water, conventionally ~0.9% NaCl by weight for normal saline. Classical solute-solvent theory states that the salt (solute) will dissociate in water (solvent) to form NaOH and HCl in equilibrium. Thus the actual energy is not absorbed by a "salt" ion at all, but rather by the acid-base equilibrium ions in coexistence within the solution media.

From these examples, it is hypothesized, again without wishing to be bound by theory, that many of processes heretofore described as resulting from a "plasma" actually are a result, at least in part, of oxy-hydro combustion. The oxygen and hydrogen are created by electrolysis, with concurrent ignition, all as a result of high frequency, high voltage energy sources. The invention disclosed herein correctly explains the phenomenon heretofore described during electrosurgery observations as "arcing", "electron excitation", "molecular friction", "vapor layer", "plasma formation", "plasma streamers", or "popping". The understanding and appreciation of this disclosed mechanism of action enables further electrosurgical device and method embodiments that more accurately follow in vivo physiochemical processes and open such embodiments to new applications not previously envisioned for electrosurgical devices and methods as disclosed heretofore.

In one such embodiment, the devices and method of this invention include a means to deliver one or more gases required for combustion to a surgical site, without the need to perform electrolysis to liberate hydrogen and/or oxygen for the combustion process. In one preferred embodiment, both oxygen and hydrogen gases are provided for the combustion process, with ignition through electrode means. The gases may be in a compressed form, and optionally are metered via throttling valves and mixing chambers. The gases, such as oxygen and hydrogen, delivered via a suitable conduit to an electrosurgical device. The gases are delivered to the distal end of said device where they are ignited using a voltage source and an ignition device. The resulting combustion zone is sufficiently controllable to enable treatment of small biological structures and sufficiently scalable to permit treatment of comparatively large areas.

In another such embodiment, the devices and methods of this invention include an electrode that liberates an elemental gas, such as hydrogen, without electrolysis. Thus metal alloys and compositions wherein elemental gases are liberated upon providing power to such electrode are provided. Such metals and alloys thereof are disclosed in U.S. Pat. Nos. 5,964,968, 5,840,166, 5,746,896 and 5,494,538, incorporated herein by reference. Such compositions may be made into electrodes or similar structures that liberate elemental gas, such as hydrogen, when subjected to an electric current. Use of these metals in the active electrode provides an enriched combustible gas environment, thereby fostering more rapid and intense oxy-hydro combustion. In addition, the use of such materials reduces reliance on electrolysis to produce combustion gases or the need for a conduit to deliver combustion gases to the combustion site.

In yet another such embodiment, the devices and methods of this invention provide shielding to the electrosurgical device, and preferably a bipolar electrosurgical device including at least two electrode elements, whereby the shielding is employed to advantageously utilize the acid-base throttle effect of oxy-hydro precursor reactions. The shielding, which may be a telescopic sheath, may be employed to create a fluid reservoir that both limits oxy-hydro combustion via the acid-base throttle effect and further advantageously distances the active electrode from the surgical site.

Additional benefits are gained from understanding the physiochemical process involved in this phenomenon as disclosed. Further, increased knowledge is gained regarding mechanisms of patient injury observed during the application of prior art electrosurgical devices and methods that shed further light upon these processes. For example, it is known that in the prior art paradigm of electrosurgery, the electrical current flows through the path of least resistance. It is also documented in the literature that the typical nerve function disruption resulting from monopolar electrosurgery has been thought to result from heat effects of the probe through concepts described as "depth of necrosis" or "the depth of penetration of the heat", even though temperature studies have not fully borne such a conclusion. This apparent inconsistency can now be understood in that the path of damage that occurs is not one of collateral heat induced damage, but one of the physiochemical oxy-hydro combustion acid-base shift reaction disclosed herein. The alteration of the acid-base milieu that normally results from electrosurgery is clinically observable in the nervous system, since the nervous system's clinical function is most sensitive to acid-base shifts. The alteration in nerve conductivity induced by the acid-base shift is resultant from direct changes in membrane ionic function and electrical pulse propagation for nerve conduction. The normal tissue response to such an acid-base insult is to metabolically correct the disruption and resume normal function. If the effect was due to thermal damage, the healing response would be quite different and follow a different time course typical of that type of insult. Clinically, a quick resolution of function typical of metabolic alterations (short effective refractory period of membrane responsiveness) is observed, rather than that of thermal damage (prolonged effective refractory period of membrane responsiveness). Acid-base buffering systems of the body fluids provide the most immediate defense against changes in acid-base environment and provide an important response to treatment. Phosphate and bicarbonate buffers are examples of these systems that function locally. Each acid-base or metabolic/structural disturbance is followed by the tissue's response to such a disturbance, and this response can be used for therapeutic protocols. The complete effect of electrosurgical oxy-hydro combustion acid-base shift tissue treatment within the body goes beyond heat alone, and includes more profound metabolic alterations induced by the acid-base shift phenomenon as well as the host organism responses induced by the device and method of application.

The physiochemical processes disclosed herein further reconcile the use of a typical electrosurgical probe in the ambient air, underwater, cellular, and/or biologic environment to produce sufficient heat and other metabolic effects for the efficacious application of energy to biologic tissue structures as part of the ablative, coagulation, modification, or other surgical processes. The general functions of these probe embodiments are those of a tissue modifier, such as by coagulation or cutting, that induce a healing or reparative host response. In the coagulative lower relative energy function, for example, the dominant physiochemical reaction is initial electrolysis reaction 10. In this mode of operation, a typical electrosurgical probe produce localized acid-base pair equilibrium at an elevated temperature due to the heating effects of the active electrode resistive heat transfer to the solution. Metabolic affects are important in vivo with such application. As the amount of energy delivered to the active electrode is increased, the energy delivered to the oxy-hydrogen co-mingling gases becomes sufficient to ignite the oxy-hydro combustion reaction and sustain electrolysis simultaneously with both reactions 10 (FIG. 1) active in this overall process. This process describes a cutting function of electrosurgical devices. However, in no instance has a plasma been formed.

This graded effect as described by FIG. 1 also explains other electrosurgical observations. For example, there exists a transitional power input where the energy delivered to the active electrode cannot sustain a sufficient electrolysis rate to support continuous oxy-hydro combustion. This results in what is frequently observed as a "popping" operation of an electrosurgical probe. In this mode of operation the combustion process consumes the available co-mingling gas volume through the combustion reaction, thereby producing water, resulting in collapse of the gas volume and quenching the thermal energy delivered by the active electrode. As a result the active electrode is cooled and for a transient period there is insufficient gas volume or heat to sustain an oxy-hydro combustion. Electrolysis necessarily must then reestablish the gas volume necessary to sustain the oxy-hydro combustion reaction. As energy input to the electrode is increased the rate of electrolysis becomes sufficient to prevent the collapse of the oxy-hydrogen gas volume as the combustion reaction takes place, and continuous oxy-hydro combustion is sustainable. In another such embodiment of the invention, exploitation of the acid-base throttle can be used to control the direction and magnitude of the physiochemical processes disclosed herein to avoid the uneven physiochemical flow evidenced by "popping".

Based upon the understanding of the hypothesized electrosurgical process set forth herein, the variations of possible processes become evident. FIGS. 1B and 1C illustrate general potential modes of operation that an electrosurgical process can embody. In this case the reaction is described by the coexistence of hydroxide and hydronium ions, which participate in the oxy-hydro combustion reaction process. The same principles that govern the salt-ion reaction process apply to the generalized case and further reveal what forms in which the overall reaction can manifest itself.

It may thus be seen that the methods and devices of this invention may be employed for electrosurgery on any living biologic tissue that is composed primarily of water, salts such as sodium chloride, and minerals in solution. The tissue changes that can be induced include tissue ablation, vaporization, coagulation, cutting, modification, and induction of host responses that are deemed therapeutic. In general, it is possible and contemplated to induce non-necrotic tissue modifications conducive to normal healing or reactive responses as an important manifestation of this disclosed electrosurgical application.

As an example, it has also been discovered and is contemplated that the methods and devices of this invention may be employed for fusing or welding bone-related tissues, such as is disclosed in pending U.S. patent application Ser. No. 09/885,749, entitled Method For Fusing Bone During Endoscopy Procedures, filed Jun. 19, 2001, and incorporated herein in its entirety. In brief, if bone fusion or welding is necessary as part of a surgical procedure, a piece of autologous bone can be harvested from another part of the body, or alternatively an allograft, synthetic composite, combination composite of synthetic and biologic origin, genetically engineered bone material or other materials containing bone-derived collagen material or a mimetic thereof, including a composite including type I collagen, is utilized. The portion of harvested bone or alternative substitute is prepared, such as by ex vivo chemical or mechanical treatment to remove or alter the mineral matrix and provide a good fusion or welding surface. Similarly, the in vivo bone contacting surfaces may optionally be treated to remove or alter the mineral matrix, and a biocompatible "de-fat" procedure is employed. The harvested bone or alternative substitute may further be modified to include an interfacing agent for the fusion or welding process.

The harvested bone or alternative substitute and/or the recipient bone may be chemically or mechanically treated to remove or alter the mineral matrix and provide a good fusion/welding surface. Because the fusing/welding occurs in a fluid medium and in vivo, any chemical utilized upon the recipient bone in particular must be safe to the human or animal and to the tissues being treated. In the case of acid pre-treatment of bone surfaces, dilution is necessary. Or, other acids or chemical compositions, friendly to the host, may be used such as acetic acid, citric acid, malic acid, or other acids found normally in human ingested foods or endogenously produced by the host organism. Generally, the harvested bone tissue is treated with demineralization procedures and the recipient bone is treated with biocompatible agents to "de-fat" the porous intersticies, such as hydrogen peroxide, evacuating those spaces to accommodate the introduction of a bioactive interfacing agent. The bioactive interfacing agent may include a biocompatible acid-treated bone-derived graft material, a carrier substance that allows use in a fluid environment, a visualization aid, a substance that channels the electromagnetic energy, and an osteinductive/osteoconductive compound or compounds. An example of such a composite would be citric acid, bone graft, hydroxyapetite, and tricalcium phosphate gel. Such configuration provides greater stability of manipulation and of placement in an in vivo fluid medium such as during endoscopy. The surfaces of the bones to be fused or welded are contacted, preferably with the interface agent positioned therebetween. Fusion or welding is by means of the devices and methods disclosed herein, preferably employing a source of radio frequency electromagnetic radiation. To those skilled in the art, it is clear that the acid-base involvement of the process disclosed herein is directly related to the relative demineralization harnessed for the bone welding process.

Thus methods and devices of the invention described herein may be employed with any of a wide variety of tissues, including without limitation any soft tissue or hard tissue, or soft tissue-derived and bone-derived products and/or materials. In the case of collagen tissues, the methods and devices can further be employed to fuse, weld or otherwise join such tissues such as for bone welding, vascular anastomosis, neurorraphy, and the like. Further, as acid-base shifts affect cell membrane permeability, such changes can be harnessed for therapeutic measures, as described hereafter.

It may further be seen that certain embodiments of the invention described herein may be employed in applications where prior art conventional monopolar devices are employed, such as in a non-conductive aqueous media of some endoscopy fluids. Even where the macro-environment, such as endoscopy fluids, is non-conductive, the micro-environment, in proximity to the electrodes and devices hereafter described and the biological tissues to be modified, is necessarily conductive. Thus the methods and devices described herein may, with such modifications as are required and will be apparent to one of skill in the art, be employed in applications where prior art conventional monopolar devices are now employed. Similarly, the methods and devices described herein may be employed in applications where prior art conventional bipolar devices are employed, such as environments wherein a conventional conductive aqueous media is employed. Further, the methods and devices described herein may be employed in applications of traditional open surgical procedures, i.e. in ambient air (versus endoscopic procedures), with the host biologic tissue itself serving as the fluid reservoir or fluid environment.

The devices and methods of this invention have been employed with a variety of solutions, including 0.9% NaCl, 0.9% KCl, $H_2SO_4$, HCl, distilled $H_2O$, and a glycine solution, and a variety of state parameters, including varied pH and temperature. Further, the devices and methods of this invention have been employed without solutions in the macro sense, and been use in "ambient" air conditions of hydrated and normal biologic tissue. In addition, a variety of RF energy settings have been employed, such as the embodiment of 150–2000 Volts peak to peak with a range of power settings between 5 and 500 Watts. Based on analysis of various solutions, states, and energy profile applications, the general equation of FIG. 1C was validated, and data obtained for the graph of FIG. 5. Although the energy input required to initiate and/or sustain a plasma markedly exceeds these levels (or any levels contemplated for electrosurgical application), even for the most favorable plasma generating conditions (refer to above ionization discussion for typically encountered constituents of a biologic system during electrosurgery), the transition from electrolysis and combustion to that of plasma formation based upon energy input has not been determined. It is anticipated that as energy level is increased, significantly surpassing the ionization potentials of the constituents of a biologic system, electrolysis and combustion would yield to plasma formation; however, this transition point far exceeds the levels of energy that an organism can withstand and is not contemplated for electrosurgery due to the significant iatrogenic injury that would be induced. The energy configurations typically employed in and contemplated for electrosurgery, and those that we have verified as discussed above, provide sufficient energy to initiate and sustain the electrolysis and combustion reactions 10 as disclosed herein, allowing for the use of such physiochemical reactions for therapeutic means as further disclosed herein.

Further, microscopic examination of various human tissue types, including ligament, articular cartilage, and fibrocartilage, was conducted both prior to and subsequent to application of RF energy at low power settings of between 5 and 40 Watts for short time durations, on the order of two to five seconds. The observed histological changes appear visually identical to those induced by changes in the acid-base state. Altered cell membrane structure and permeability, cellular osmotic states (dehydration, swelling, etc), and changes in the structural properties of intracellular organelles were evident histologically. The histological changes did not result in cellular destruction, and were compatible with inducing a healing response in the affected tissue. Normal tissue response is to metabolically correct disruptions and resume normal function. Further, it was observed that by use of a prototype probe incorporating both an active and return electrode, it was possible to induce similar changes without actually touching the tissue, thus resulting in a desired alteration without direct contact of the probe to the tissue. In one embodiment, a small funnel or cone tip on the probe permitted resulting energy to be directed toward the tissue, thereby resulting in a very small and isolated area of delivery of energy.

Use of the methods and devices of this invention permit micro-scale treatment of living tissue, without necrosis, and induce or permit a normal healing response of that tissue. It is hypothesized that by controlling the energy and reaction as generally described by the equations of FIGS. 1A to C, it is possible to provide sufficient heat energy to cells to induce natural repair mechanisms without inducing permanent injury to the cells, while maintaining an acid-base shift in the immediate cellular environment that is not unduly deleterious, and may in fact advantageously result in changes to cellular membrane permeability desired for treatment therapeutics (a derivative of the clinical nerve example above and the histological data disclosed above). Such alteration in permeability may allow introduction of other therapeutic agents which otherwise would not have been efficacious. Further, the heat application can induce gene expression of the heat shock or other class proteins typical of that induced systemically by fever. This heat induction controlling gene expression can now be induced locally by the use of the methods and devices disclosed herein.

In general, it is believed that the relationships between salt content, temperature, dissociation properties in solution, pressure, pH, energy and the like follow non-linear mathematical relationships. As discussed hereafter, application in a surgical environment necessarily is in a finite and definable reservoir. Differential equation sets may be developed to model the mechanisms described in this invention in a finite reservoir, such as for example a knee joint. Additionally, the fluid mechanics of the arthroscopic devices and methods employed in a surgical procedure may be modeled by analysis of issues such as fluid flow rate, delivery method, pressure, currents, and reservoir anatomy, such as anatomy of a joint on which a surgical procedure is performed. By varying determining and analyzing such parameters, other and further embodiments of the invention herein present will become apparent to those skilled in the art.

The process, methods, and devices disclosed herein are further elucidated via a series of experiments and additional embodiments.

Figure 8A:
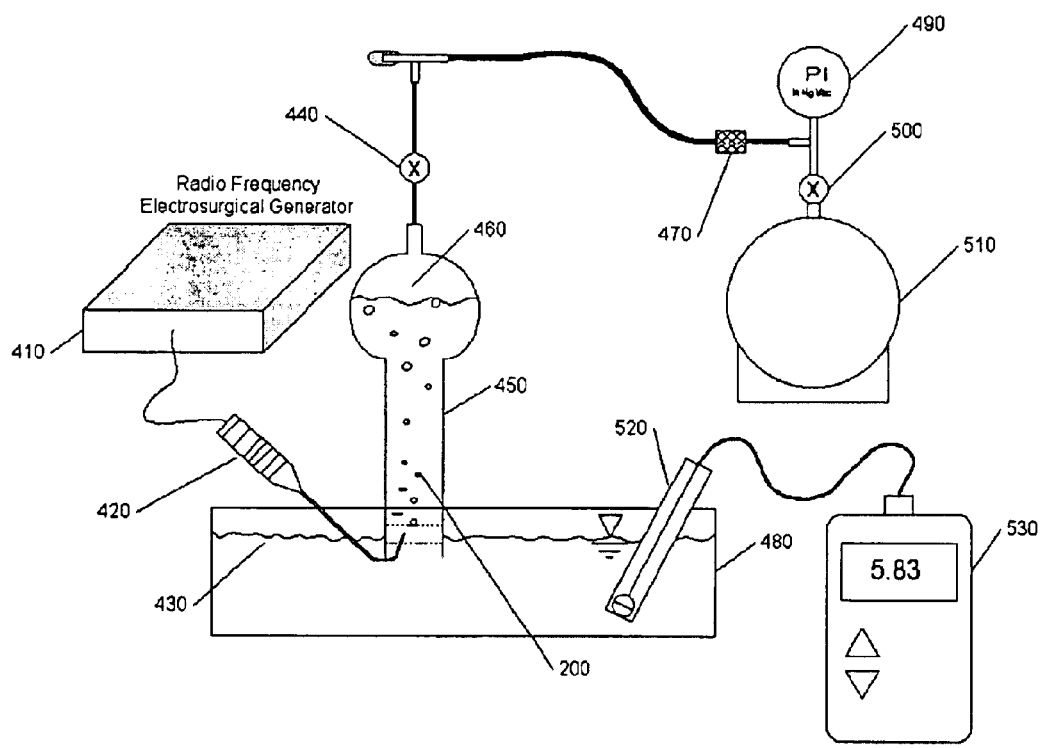
FIG. 8A depicts experimental apparatus used to determine the constituent chemical components of the electrosurgical phenomenon.

FIG. 8A depicts a device for collecting and sampling the oxy-hydrogen gas combustion reaction by-products. In experiments utilizing the apparatus shown in FIG. 8A reaction products of the electrosurgical phenomenon were collected and analyzed to determine their makeup. Gas species were analyzed to determine both make-up and relative concentrations. An apparatus for collecting the gaseous emissions from a standard bi-polar electrosurgical probe was assembled and used in a saline bath. Gas collection tube 450, was inverted and filled with 0.9% by weight saline, as was Pyrex glass solution bath container 480. The filled gas collection cylinder was then carefully stoppered and replaced in the bath to form a manometer water column that could be displaced by collected gas. Typical bi-polar electrosurgical probe 420 was bent to accommodate the gas collection tube inlet and fixed for the duration of the experiment. Gas collection tube 450 was attached to flexible tubing and then to evacuated summa canister 510 for gas sample collection. Electrosurgical console 410 was set to a maximum power output of 180 W for probe 420. Gaseous emanations were observed at the electrode tip during the "firing" of the probe. Bubbles 200 naturally floated up into capture section 460 of tube 450 because of buoyancy forces and were allowed to accumulate and displace approximately 95% of the total volume of the tube. When the tube was filled to maximum capacity the firing of the probe was stopped and the gas carefully evacuated from the top of tube 450 via means of partially opening stop-cock valve 440 to form a restriction, and sequentially opening needle valve 500. The combined flow restrictions created by valves 440, 500 and flow restrictor/filter 470 made metering of the inlet of the gas rate manageable to avoid unwanted water uptake by summa canister 510. The process of firing the probe, capturing the gaseous emanations, evacuating off the filled tube and filling the summa canister was repeated six times to capture approximately a total of 180 ml of gas in the summa canister. The canister was left with partial vacuum intact by using pressure gauge 490 to determine the final negative pressure. This pressure was checked by the receiving laboratory to ensure that inadvertent uptake of contaminating atmosphere has not happened during transport of the canister to the examining laboratory. The gas was subsequently analyzed for $N_2$, $H_2$, CO, $CO_2$, $CH_4$, $C_2H_6$, and $C_2H_4$. laboratory analysis showed a near perfect ratio of 1.933:1, hydrogen to oxygen, in agreement with the equations of FIG. 1. In a second experiment the presence of acid-base pairs in the solution remaining after combustion was examined. This was accomplished by using pH meter 530 in conjunction with dielectric pH probe 520 to take a baseline measurement of salt solution 430, with periodic measurements as the experiment progressed. Solution bath 480 represents a finite reservoir of solution and thus the increasing molarity of salt-ion solute should have the effect of increasing acidity of the bath 480. In fact, experimental data show a nominal shift of approximately 2 pH acid, which confirms the presence of acid-base pairs as predicted by the stoichiometry.

Chemical analysis yielded findings that support the stoichiometry shown in FIGS. 1A and 1B. Hydrogen and oxygen gases were found to be present in exactly a 2:1 ratio as shown in 30.

Figure 2:
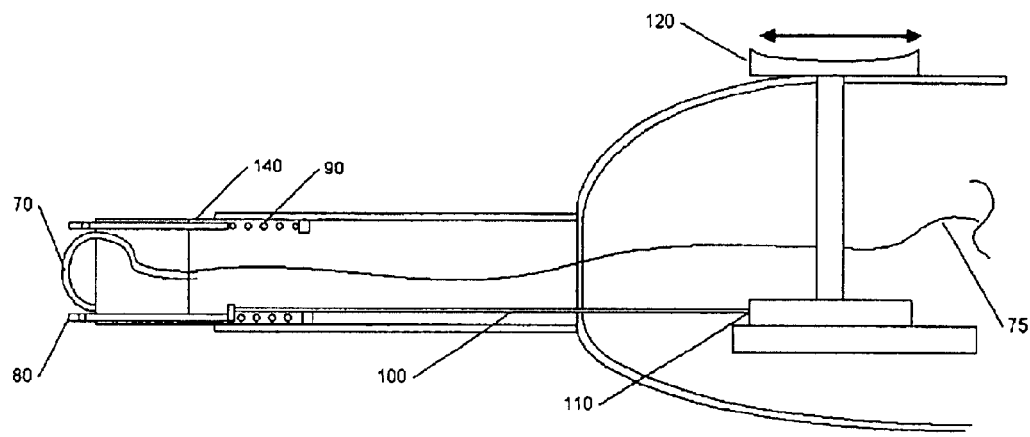
FIG. 2 is a view of an electrosurgical probe with a retractable sheath to create a fluid chamber that activates the acid-base throttle effect of oxy-hydro combustion in an aqueous ionic solution.

FIG. 2 is a view of a preferred embodiment of an acid-base throttle sheath probe used in the underwater, cellular and biologic electrosurgical environment. Translating sheath 80 is employed to create an acid-base trapping zone and thereby harness the acid-base "throttling" effect of lowering the available moles of electrolyzed oxy-hydrogen gas, thereby reducing the net heat of reaction in the oxy-hydro combustion. Translating sheath 80 extends itself beyond the most distal portion of active electrode 70 to form a plenum chamber wherein acid-base pairs are allowed to collect and decrease the reactants of oxy-hydro combustion. Current flows between active electrode 70 and return electrode 140 to complete the electrical circuit. Sheath 80 can be selectively positioned by using sliding ratcheting finger switch 120 via coupler guide stanchion 110 and push-rod 100 to set the desired quantity of acid-base entrapment and tune the rate of reaction observed at active electrode 70. Active electrode lead wire 75 is constructed to have sufficient slack within the probe body that translation of active electrode 70 is not constrained by connected lead wire 75. Sheath return spring 90 is tensioned by translation of push rod 100 as sheath 80 is extended to its most distal position, and is retained by finger switch ratcheting mechanism 120. When released, sheath 80 is pulled by return spring 90 into its normally proximal position.

Figure 2A:
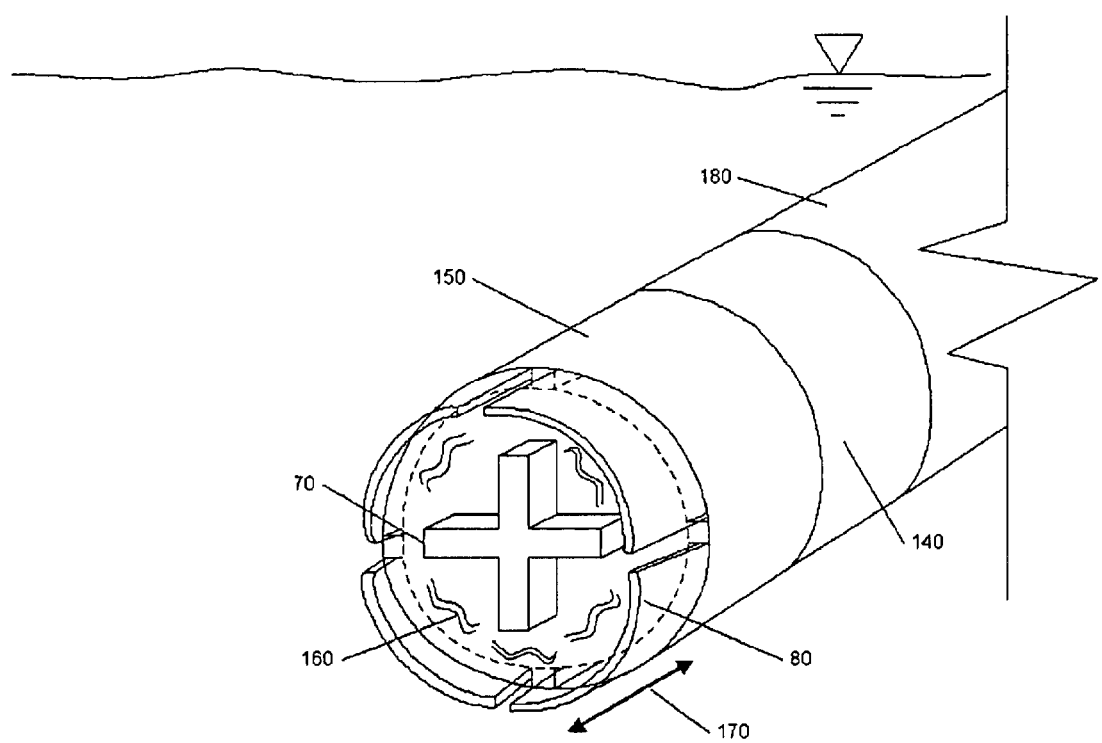
FIG. 2A is an isometric view of the retractable sheath of FIG. 2 disclosing a fluid chamber that activates the acid-base throttle effect of oxy-hydro combustion in an aqueous ionic solution.

FIG. 2A illustrates another view of a preferred embodiment of the acid-base throttling sheath. In this view acid-base throttle sheath mechanism 80 is in the distally extended position. Freedom of travel is shown by translation direction arrows 170. The electrical circuit is completed between active electrode 70 and return electrode 140. Both the active and return electrodes are conductively isolated from each other using thermal and electrical insulator 150 which may preferably be constructed of a ceramic or high temperature polymer. The remaining area of the return electrode is insulated by insulating sheath 180. As depicted, the energy applied to the probe is only sufficient to generate electrolysis and is fully consumed by said reaction. Insufficient excess energy exists to ignite the co-mingling oxy-hydrogen gases and thus only the products of the first of reactions 10 are created. During typical application of low-level RF energy acid-base pair density streak lines 160 are plainly visible to the naked eye; these are byproducts of the electrolysis reactions known to govern the overall process.

The translating sheath 80 may be cylindrical, as depicted, or may be conical, or may alternatively have a conical or cone tip. In this way, the size of the probe may be reduced, and the shape or configuration of the electrodes and sheath may be such as to direct energy in a desired pattern or manner, so as to provide maximal energy delivery to a discrete area to be treated, while minimizing injury to adjacent tissues. Similarly, in this way energy may be directed to the area to be treated without the probes or electrodes actually contacting such area.

In the operation of the preferred embodiment of FIGS. 2 and 2A the oxy-hydro combustion process is mechanically adjusted to suit the desired intensity of operation. Active electrode 70 generates the oxy-hydro combustion reaction, while translating sheath 80 can be positioned to create a convection trap for acid-base pairs 160 generated as part of the oxy-hydro combustion reaction process. Increasing the concentration of the acid-base pairs reduces the net available oxygen and hydrogen gases that can be generated by the electrolysis reaction. This, in turn, leads to a decreased intensity of the overall reaction. This effect is defined herein as the acid-base throttling effect on the oxy-hydro combustion reaction process. The translation of sheath 80 alters the conducted electrical pathway of the RF energy. The sheath, when constructed of a non-metallic substance, does not alter the transmission pathway. By positioning the sheath using ratcheting finger slide 120, coupler guide stanchion 110 and push-rod 100 in combination the oxy-hydro combustion reaction can be trimmed to the most desirable level of intensity. Additionally, in surgical modes of operation where no tissue contact is desired the throttling sheath can be used to fix the distance to the tissue and provide a consistent tissue treatment benchmark distance. When combined with manipulation of delivered power to the active electrode, a precise control of both the oxy-hydro combustion reaction and the surgical process can thus be achieved.

Figure 3:
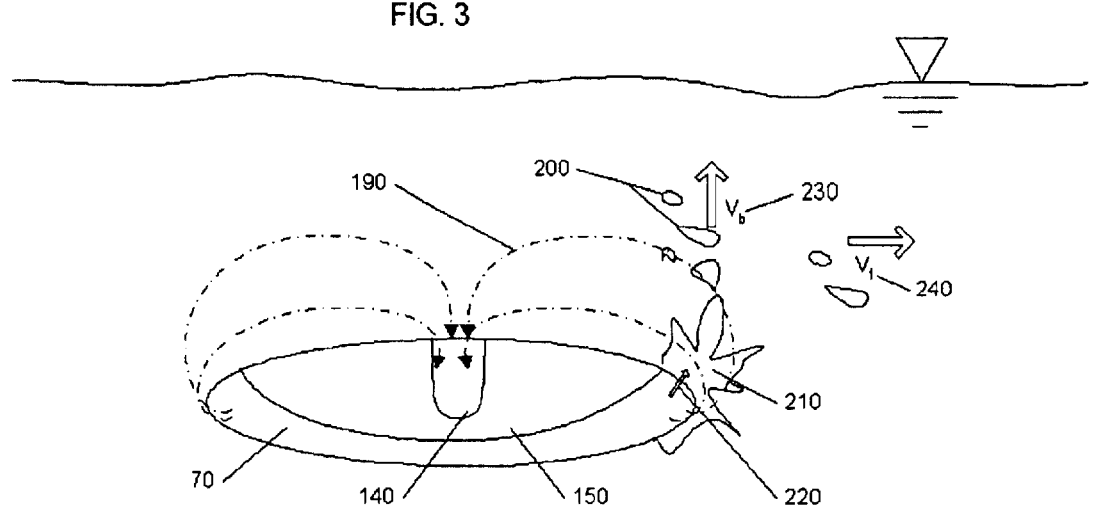
FIG. 3 is a view of an electrosurgical electrode utilizing a metal alloy that releases elemental gases upon excitation by electric current.

FIG. 3 is a preferred embodiment wherein the active electrode contributes elemental gases to the oxy-hydro combustion reaction. This embodiment illustrates the case where sufficient excess RF energy is imparted to the electrolyzed gas to ignite the mixture, reduce the reactants, and release heat and light. In this case, active electrode 70 is manufactured from an elemental gas-storing metal alloy, such as those disclosed in U.S. Pat. No. 5,964,968, that is used to enrich the electrolyzed gas process and facilitate an increased rate of reaction. Active electrode 70 releases elemental gas 220 such as hydrogen or oxygen, optionally upon electrical excitation by RF energy. This energy is used to complete the electrical circuit between active electrode 70 and return electrode 140, separated by insulator 150, via current flow 190. Oxy-hydro combustion zone 210 is thereby enriched with excess gaseous reactant and can more readily accommodate combustion even in the rapidly fluctuating, semi-quenched, fully-immersed environment. Normal heating effects due to the conducted portion of the absorbed energy from current flow 190 cause immediate density changes in addition to an acid-base shift that allow for the oxygen and hydrogen gases to escape combustion zone 210 without being ignited. The buoyancy created by the density change has a resultant velocity vector 230 that governs the rate of gas escape, and in normal electrosurgery the entire field of surgery is normally kept under constant flow with velocity vector 240.

Active electrode 70 can release any desired elemental gas, but in a preferred embodiment the elemental gas released is hydrogen. One exemplary alloy that may be employed is a magnesium alloy capable of inducing generation of hydrogen when reacted with water in the presence of a salt containing chlorine, the alloy containing between 0.4% and 10% by weight nickel and between 0.015% and 10 by weight zinc, as disclosed in U.S. Pat. No. 5,494,538. Another exemplary alloy that may be employed is a rare earth metal-nickel hydrogen storage alloy, including the alloys disclosed in U.S. Pat. Nos. 5,840,166 and 5,964,968. In general, hydrogen releasing rare earth alloys of the $AB_5$ type are known, containing light rare earth elements such as La, Ce, Pr, Nd or mixtures thereof in the A site, and Ni, Co, Mn, Al or mixtures thereof in the B site. These alloys permit hydrogen adsorption and desorption, optionally in response to application of energy, such as RF energy.

In the operation of the embodiment of FIG. 3, the electrode thus supplements gas production, and preferably hydrogen production. The active electrode is comprised of a material that enriches and/or enhances the overall oxy-hydro combustion reaction. Under ordinary underwater, cellular, and biologic electrosurgical conditions when electrolysis takes place natural buoyancy 230 of the generated gas is augmented by heating effects of active electrode 70 and thereby increases net buoyancy forces acting on the gas. This condition generally contributes to an accelerating of the gas away from the active electrode. To further exacerbate the problem the normal mode of operation of underwater, cellular, and biologic electrosurgery is usually done in a flowing environment, which imparts a flow velocity vector 240 to the overall fluid field. To counteract the amount of "lost" gas from both bubbling off and flow, a means is provided whereby immediate oxy-hydro combustion zone 210 can be enhanced with elements that contribute to the oxy-hydro combustion reaction process. As RF current energizes active electrode 70 a release of elemental gas 220 takes place directly into the co-mingled oxygen and hydrogen gas combustion zone. This augmentation of the ongoing electrolysis reaction can be used as a quenching element by providing excess gas, thereby reducing the net combustion heat output. Alternatively, the augmentation by liberated gas 220 can be used to optimize stoichiometry, thereby optimizing and maximizing oxy-hydro combustion heat output.

The amount of liberated elemental gases, such as hydrogen, may be determined and adjusted as appropriate for a specific treatment purpose. For microprobes employed in cellular applications, even very small amounts of additional hydrogen provide fuel theoretically adequate for a cellular response.

Figure 4:
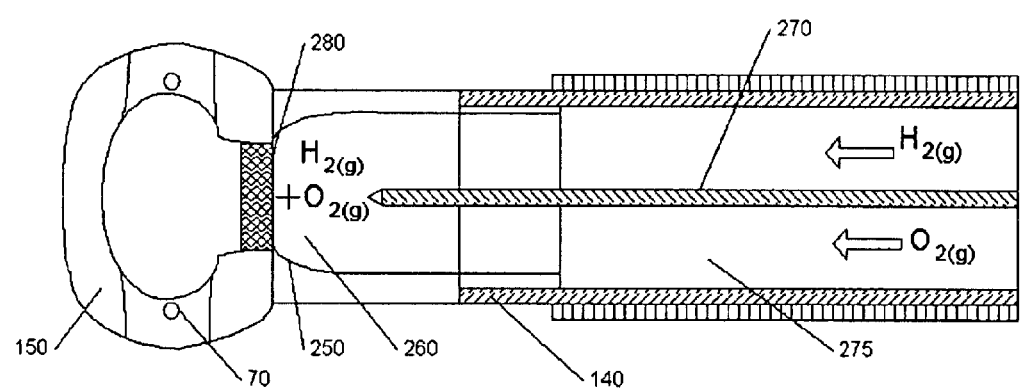
FIG. 4 and FIG. 4A are top and side views, respectively, of an electrosurgical probe providing conduits for directing the flow of elemental oxygen and hydrogen gases, a co-mingling plenum, and ignition electrode to ignite the oxy-hydro combustion process.
Figure 4A:
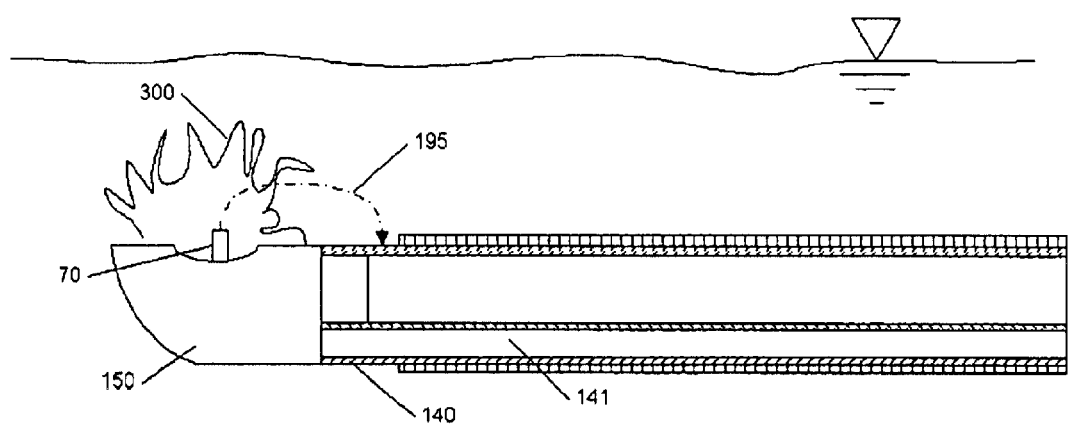

FIG. 4 and FIG. 4A depict a preferred embodiment wherein independent gas flow lumens are provided for the delivery of elemental gases to the probe tip. In this embodiment an electrosurgical oxy-hydro probe provides means for independent delivery of elemental oxygen and hydrogen gas to the probe distal tip reaction zone. Elemental gases are pressure-driven through gas transmission lumen sections 275 separated by gas conduit wall section 270 to prevent premature co-mingling of the elemental gases. Upon exit from the lumen sections the gases are mixed in plenum chamber 260 to facilitate combustion reaction process. The gases are then accelerated through converging nozzle section 250 to enhance dynamic pressure, thereby driving the oxy-hydrogen gas through flame arrester 280. The gas is then channeled upward through insulator 150 toward active electrode 70 to initiate the oxy-hydro combustion reaction process. In this specific embodiment the need for an electrically conducting irrigant is completely eliminated. FIG. 4A illustrates the separation of the electrical circuit power delivery conduction portion of the probe in isolated electrical channel lumen 141. Active electrode lead wiring traverses the lumen length to the distal portion wherein it is electrically connected to active electrode 70 and can complete a transmission circuit via electromagnetic transmission field lines 195 across insulator portion 150 to return electrode 140. Oxy-hydro combustion zone 300 is created by the ignition of the co-mingled gases being forced from the electrosurgical probe distal tip under fluid pressure. The rate of reaction can be governed by metering of the flow rate of the individual elemental gases or by "starvation" of either elemental gas to run the reaction sub-stoichiometrically "lean" or "rich", which will alter the net heat of reaction according to normal principles of combustion reaction chemistry.

The operation of this embodiment illustrates how the need for a liquid irrigant medium can be completely eliminated. Pressurized elemental oxygen gas and hydrogen gas are independently delivered to probe tip insulator 150 via isolated lumen section 275 and after mixing are ignited by heat generated at active electrode 70 from solid/fluid interface transmission wave generation heating. The intensely hot flame generated can be used for a variety of purposes in a surgical setting. Additional advantages in this specific mode of operation become evident. The power needed to ignite the co-mingling oxy-hydrogen gas mixture is reduced because the conducted portion of the energy needed to electrolyze is now no longer necessary. Only that portion of the energy that provides heating to the active electrode sufficient to ignite the mixture is necessary to sustain the combustion. FIG. 4A illustrates uses in conjunction with a fluid irrigant that provides further enhancing capability to the oxy-hydro combustion reaction process. In many cases having intense heat sources within the human body is undesirable, and use of an irrigant can provide multi-faceted additional advantages, the most apparent of which is as a quenching media to reduce collateral heat transfer to healthy tissue structures. Such an irrigant is preferably composed of acid buffering agents that form a solution resistant to change in pH when either acid or base is added, such as from the natural process of oxy-hydro combustion.

FIG. 5 depicts the general energy absorption curve for the electrolysis and ignition of the oxy-hydro combustion reaction process. The curves depicted show the multi-dimensional aspects of the immersed environment and how they affect the overall combustion process. It is important to understand that the net energy consumption of the entire process consists of two distinct components of RF energy, conduction and transmission. Conducted energy 320 is consumed in the molecular electron transfer between ions in solution. Transmitted energy 310 involves the electromagnetic wave function that is typically involved with radio-wave transmission. Both elements are present in ambient air, underwater, cellular, and biologic electrosurgery and contribute separate and discrete energy functions to the overall process. As shown in FIG. 5 the mode of energy consumed is dependent on the relative concentration of salt ion in solution. As the salt ion concentration approaches zero the bulk of the energy is consumed through conduction as pure water is only moderately conductive. Some transmission 310 actually occurs at all states and is therefore shown as a smaller portion of the overall energy consumed. As salt ion concentration increases the solution resistivity drops and the amount of energy consumed through conduction 320 also drops. Sufficient resistivity of the solution media remains that heating takes place as part of the conduction process, but the active electrode being heated by its own metallic resistance at the liquid-metal interface delivers the majority of the heat generated prior to ignition of oxy-hydro combustion reaction. As the salt ion concentration continues to increase, conduction resistivity continues to drop until a relative minimum of conduction resistivity 340 is achieved. At this point in oxy-hydro combustion energy absorption process curve 330 the majority of the energy consumed is through transmission 310. In all cases the curve defines the total energy input for which oxy-hydro combustion ignition can be achieved. However, at the optimum salt ion concentration point 340 the minimum amount of input energy is required to both electrolyze the solution and ignite the oxy-hydro combustion reaction.

If the salt ion concentration is increased further still, while holding the solution temperature constant, a partial fraction of solid salt ion will co-exist as a suspension, the overall solution having reached saturation limit 370 for the given temperature. Curve portion 360 illustrates the energy absorption required for oxy-hydro combustion ignition as the partial fraction of salt ion is increased beyond saturation limit 370 for the solution. As the salt ion concentration is increased beyond saturation limit 370 along curve 360, both conduction and transmission resistivity are generally increased and the net energy required to achieve oxy-hydro combustion ignition is also increased. Curve 350 illustrated the shift in solubility created by increasing solution temperature. Temperature rise in solvent is known to increase solute capacity; this condition is commonly referred to as "super-saturation." As the solution is heated, whether artificially or purely by conducted heating from the active electrode, the energy required for oxy-hydro combustion is increased. From equations 10, it can be seen that this is a result of greater concentration of salt ion fraction in the equilibrium state of acid-base pairs, which reduce the net amount of water that can be electrolyzed into oxygen and hydrogen gases. This specific condition is an artifact of a finite reservoir. In many surgical situations, as the fluid is in constant flow there is no excessive buildup of acid-base pairs, since they are "flushed" away in the flowing solution.

It can be appreciated from the chart in FIG. 5 that the acid-base throttle effect can be overcome through the addition of RF energy as the concentration of acid-base in solution rises. This is most advantageous in understanding why maintaining an optimum flow throughout the surgical field proves beneficial in electrosurgery. Too much flow and the heated buoyant gas escapes more rapidly than it can be combusted and becomes useless to the surgical process. On the other extreme too little or no flow leads to excessive heating and build-up of acid-base that can have deleterious tissue effects if left to accumulate for an extended period, including tissue and nerve damage or necrosis. The graph reveals that the solution temperature will have an indirect performance effect in allowing probe operations that vary widely from the optimum energy minima of concentration point 340.

Figure 6:
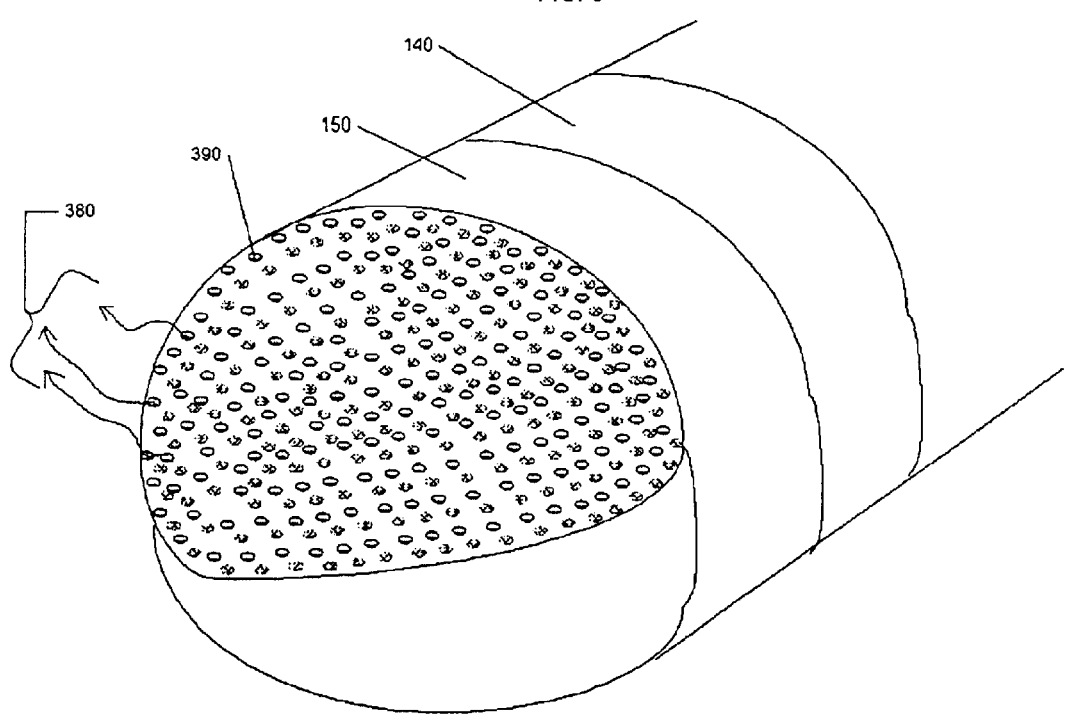
FIG. 6 is a view of a porous electrode used to meter the flow of oxygen, hydrogen or co-mingled enriching gases.

FIG. 6 is a view of an embodiment wherein the active electrode includes a porous gas-liberating alloy. Elemental gas is delivered under positive pressure to active electrode 390 and forced through pores in the conductor. The enriching gas stream exits in diffuse gas stream 380 and enters the oxy-hydro combustion zone. Electromagnetic energy is sufficiently imparted to the combustion zone to liberate elemental gas from the electrode alloy and ignite the enriched co-mingled mixture. The electromagnetic energy is delivered in transmission from active electrode 390 to return electrode 140, which is both thermally and electrically insulated by insulator 150. Insulator 150 can preferably be made from high temperature refractory ceramics or ceramic alloys. Elemental diffuse gas stream 380 is comprised of molecular hydrogen gas, molecular oxygen gas, or co-mingled oxygen and hydrogen gases to enrich the oxy-hydro combustion zone.

In mode of operation of the device of FIG. 6, several of the independent elements have been combined into a configuration of an electrosurgical probe including porous active electrode 390, which may but need not include a gas-liberating alloy, to enhance the oxy-hydro combustion reaction process. Probe activation is enhanced by forcing elemental gas 380 through the pores of active electrode 390 into the oxy-hydro combustion zone for either quenching or maximizing heat of the oxy-hydro combustion reaction. The pores of active electrode 390 allow multi-variate functions, including metering, mixing and directing the elemental enriching gases to the combustion zone. This embodiment provides improved fluid dynamics at the surface of active electrode 390, including a laminar flow of the ejecting gas or gases, more even distribution of the gas or gases and rapid thermal quench characteristics. When operated in underwater, cellular and biologic surgical environments the embodiment of FIG. 6 provides means for improving the combustion zone dynamic volume by preventing pressure field variations from forcing the collapse of the gas volume and quenching the electrode, thereby preventing oxy-hydro combustion. By supplying a uniform gas field immediately above the active electrode the gas volume is created as much by the flowing of the pressurized gas as by the electrolysis of the salt ion solution. This lowers the net power required to achieve ignition of the gas mixture and provides means for operating at much lower power levels, until a spike of energy is applied whereupon a pulse of oxy-hydrogen gas is supplied to active electrode 390, creating conditions for an oxy-hydro combustion reaction cascade. From this description it will become apparent to those skilled in the art that many dynamic controls can be used to govern the flow of gas in concert with the power output delivered to the active electrode to achieve novel effects in the oxy-hydro combustion zone.

Figure 7:
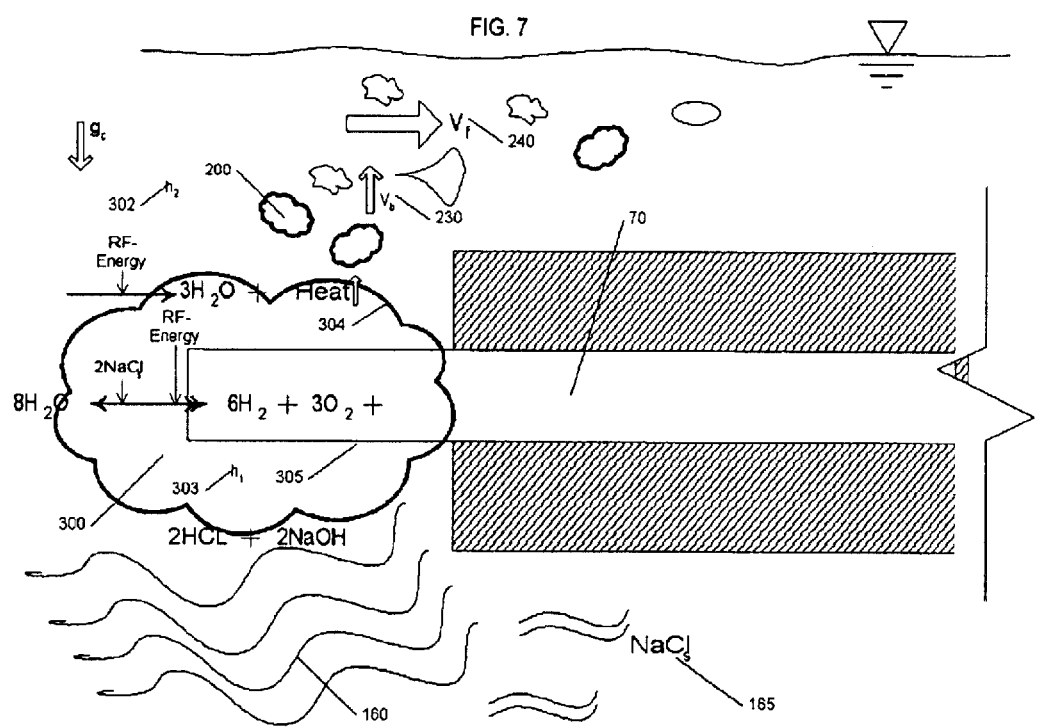
FIG. 7 is a view of the generalized flow in a salt-ion aqueous environment including the physiochemistry of oxy-hydro combustion.

FIG. 7 view illustrates a more complete, but still somewhat idealized, summary of electrosurgical oxy-hydro combustion in a sodium chloride (NaCl) salt ion solution. In this case, sufficient RF energy is imparted to the solution such that the rate of electrolysis sustains oxy-hydro combustion as shown by the overlaid equations on the representation of the physical flow-field. Active electrode 70 provides conducted RF electrical energy to active electrode solid/fluid interface 305. As the RF energy is conducted through the salt ion solution, electrolysis causes the accumulation of oxygen and hydrogen gases immediately about active electrode 70. At active electrode solid/fluid interface 305, the RF energy is transmitted through a multi-phase environment consisting of oxy-hydrogen gas and a fluid/fluid interface of oxy-hydrogen gas to salt ion solution 304. Given a constant power output to active electrode 70 the resistive heating of the active electrode material does not change. What does change is net heat transfer coefficient 303 ($h_1$) of the fluid immediately surrounding the active electrode. It is known that overall heat transfer coefficients for gases are significantly lower than those of liquids. Thus, active electrode solid/fluid interface 305 experiences a significantly lower heat transfer coefficient than fluid/liquid interface 304 heat transfer coefficient 302 ($h_2$), while the power load being applied remains constant. The consequence of this is a rapid and extreme temperature rise of the active electrode surface. As the temperature of the active electrode surface rises it imparts this heat directly to the co-mingled, accumulated oxy-hydrogen gas 300 immediately about the electrode, causing it to ignite and reduce itself to water and heat/light. This is the essence of the oxy-hydro electrosurgical combustion process. As the reaction takes place at elevated temperatures needed for ignition of the oxy-hydro combustion reaction and the co-mingled gases are of low density in relation to the salt-ion solution, buoyancy forces 230 allow for escape of uncombusted oxy-hydrogen gas. This escape is further facilitated by normal fluid flow 240 in the surgical environment. Additionally, acid-base pairs formed during the initial electrolysis reaction are of greater density than water and therefore descend away from combustion zone 300. Artifacts of the acid-base pair's existence are visible in the acid-base pair density streak-lines 160. However, since the solution temperature is near the boiling point of water, localized super saturation has taken place at fluid/liquid interface 304. As the acid-base pairs move away from combustion zone 300 cooling takes place, which results in a normal precipitation of solid sodium chloride salt 165. In a flowing environment this precipitation may never take place within the joint-space reservoir, but is visible in a static finite reservoir condition.

The two heat transfer coefficients 302, 303 are among the more dominant of the variables interacting with the system, determining the rate of heat transferred to general flow-field and oxy-hydrogen gas/electrode interface 305. This variable is a key determinant in the ignition point of the oxy-hydro combustion reaction because it is the determinant of the rate of temperature rise on the surface electrode as the oxy-hydrogen gas volume surrounds active electrode 70. Of importance is the most likely point of ignition within oxy-hydro combustion zone 300, which is in the laminar boundary layer near the surface of active electrode solid/fluid interface 305. While it may be obvious that the flame front travels outward from the active electrode, what is less obvious is how the combustion zone quenches itself both during and after combustion occurs, generating water vapor, in the form of steam. This vapor has a transient nature and coefficient of heat transfer that is greater than either coefficient 302 or 303 and therefore can transfer its heat far more effectively to the salt ion solution surrounding the transient steam pocket at the fluid/liquid interface 304 immediately after oxy-hydro combustion occurs. A corresponding volume change takes place as the combustion reaction completes. In going from oxygen and hydrogen gas to water vapor a nearly 10× volumetric change takes place, collapsing the combustion zone volume and almost instantaneously quenching and condensing the transient steam products of oxy-hydro combustion back into liquid water, which is quickly absorbed by the salt ion solution. The entire process of electrolysis and combustion is thus ready to begin anew.

FIG. 8 illustrates the more general case of variable chloride negative ion-based compound 400, which can be made up of any of Group I, period 1–7 elements on the periodic table. In this case, a chloride based acid (XCl) acts as the throttle on the overall rate of reaction. It becomes clear how the salt component of the salt ion solution contributes primarily to post oxy-hydro combustion solution neutralization/buffering. Combustion zone 300 is essentially identical in all variations of the salt ion cases, with no noticeable variation in the production of $H_2$ gas. The general case illustration demonstrates how the hydrolyzed Group I ion 306 participates in the stoichiometry of electrolysis. Acid density streak-lines 160 are still visible, as hydrochloric acid production is a normal byproduct of oxy-hydro combustion. By understanding the underlying physiochemistry, multiple possible configurations for salts become possible, including but not limited to calcium-chloride salt ion solutions, magnesium-bromide salt ion solutions, magnesium-iodide salt ion solutions, potassium-iodide salt ion solutions, potassium-chloride salt ion solutions, lithium-bromide salt ion solutions, and lithium-chloride salt ion solutions.

Other useful combinations will become apparent to those skilled in art from the disclosures above for additional salt ion solutions that will provide the necessary elements for oxy-hydro combustion. To demonstrate the general case a simple mixture of hydrochloric acid was prepared in water and a typical electrosurgical probe immersed and fired. Bubbling 200 was noted as in FIG. 8 and an oxy-hydro combustion zone 300 was created and sustained for several minutes.

The preceding examples can be repeated with similar success by substituting the generically or specifically described devices, reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of performing an electrosurgical procedure on a patient, the method comprising:
    providing a surgical probe including an active electrode and a return electrode separated by an insulator;
    providing an aqueous salt ion environment at the location wherein the electrosurgical procedure is to be performed, the environment comprising sufficient volume to permit immersion of at least the portion of the surgical probe including the active electrode and return electrode; and
    applying current to a circuit comprising the active electrode and return electrode, the current being less than that required to induce plasma ionization, but sufficient to induce electrolysis of a portion of the aqueous salt ion environment, thereby producing hydrogen and oxygen, and to further initiate a hydrogen and oxygen combustion reaction.

2. The method of claim 1, wherein the active electrode further comprises an alloy that induces release of hydrogen.

3. The method of claim 2, wherein the alloy is a member selected from the group consisting of a magnesium alloy and a rare earth metal and nickel alloy.

4. The method of claim 1, wherein the aqueous salt ion environment comprises a salt ion selected from the group consisting of sodium chloride, calcium chloride, magnesium bromide, magnesium iodide, potassium iodide, potassium chloride, lithium bromide and lithium chloride.

5. The method of claim 1, wherein the current applied comprises a high frequency voltage difference.

6. The method of claim 5, wherein the high frequency voltage difference applied comprises radiofrequency (RF) energy.

7. The method of claim 1, wherein the insulator comprises an electrical and thermal insulator.

8. The method of claim 1, wherein the aqueous salt ion environment comprises naturally occurring biological fluids of the patient.

9. The method of claim 1, wherein the aqueous salt ion environment comprises an exogenous aqueous salt ion solution.

10. A method for inducing a therapeutic response in living tissue while minimizing deleterious acid-base shifts in the living tissue, the method comprising:
    providing a probe including an active electrode and a return electrode separated by an insulator, the active electrode being disposed within an elongated lumen;
    providing an aqueous salt ion solution at the site wherein the therapeutic response is desired, the solution comprising sufficient volume to permit immersion of at least the portion of the probe including the active electrode disposed within an elongated lumen and the return electrode;
    positioning the active electrode in close proximity to the location wherein the therapeutic response is desired, the active electrode and return electrode being immersed in the aqueous salt ion solution; and
    applying a high frequency voltage between the active electrode and return electrode, the voltage being less than that required to induce plasma ionization.

11. The method of claim 10, wherein acid-base shifts resulting from application of the high frequency voltage are partially contained within the lumen.

12. The method of claim 10, wherein the active electrode and return electrode separated by an insulator are disposed within the elongated lumen.

13. The method of claim 10, wherein the position of the active electrode along the long axis of the lumen is adjustable.

14. The method of claim 13, further comprising controlling the desired therapeutic response by adjusting the position of the active electrode along the long axis of the lumen.

15. The method of claim 10, wherein minimal tissue necrosis is induced at the site wherein the therapeutic response is desired.

16. The method of claim 10, wherein the active electrode further comprises an alloy that induces release of hydrogen.

17. The method of claim 16, wherein the alloy is a member selected from the group consisting of a magnesium alloy and a rare earth metal and nickel alloy.

18. The method of claim 10, wherein the aqueous salt ion solution comprises a salt ion selected from the group consisting of sodium chloride, calcium chloride, magnesium bromide, magnesium iodide, potassium iodide, potassium chloride, lithium bromide and lithium chloride.

19. The method of claim 10, wherein the high frequency voltage comprises radiofrequency (RF) energy.

20. The method of claim 10, wherein the insulator comprises an electrical and thermal insulator.

21. The method of claim 10, wherein the therapeutic response comprises a member selected from the group consisting of nerve ablation, tissue ablation, tissue cutting, tissue coagulation, tissue modification, and induction of host healing response.

22. A method for decreasing tissue necrosis at a site wherein high frequency voltage is applied to an active electrode immersed in an aqueous salt ion solution, the method comprising the steps of:

provided an active electrode movably disposed along the long axis within an elongated lumen;

immersing the active electrode in an aqueous salt ion solution; and applying a high frequency voltage to the active electrode;

wherein the active electrode movably disclosed along the long axis within the elongated lumen defines a plenum chamber, the method further comprising minimizing the acid-base shift at the site by varying the volume of the plenum chamber by adjusting the position of the active electrode along the long axis of the lumen.

23. The method of claim 22, further comprising the step of adjusting the active electrode position along the long axis such that the acid-base shift at the site does not cause deleterious alterations in tissue at the site.

24. The method of claim 22, wherein high frequency voltage less than that required to induce plasma ionization is applied.

* * * * *